US007811321B2

(12) United States Patent
Reynolds

(10) Patent No.: US 7,811,321 B2
(45) Date of Patent: Oct. 12, 2010

(54) METHODS OF PERFORMING EMBOLISM-FREE VERTEBROPLASTY AND DEVICES THEREFOR

(75) Inventor: Martin A. Reynolds, Mansfield, MA (US)

(73) Assignee: DePuy Products, Inc., Warsaw, IN (US)

( * ) Notice: Subject to any disclaimer, the term of this patent is extended or adjusted under 35 U.S.C. 154(b) by 733 days.

(21) Appl. No.: 11/207,356

(22) Filed: Aug. 18, 2005

(65) Prior Publication Data

US 2006/0052743 A1    Mar. 9, 2006

Related U.S. Application Data

(62) Division of application No. 10/301,451, filed on Nov. 21, 2002, now Pat. No. 6,979,352.

(51) Int. Cl.
*A61F 2/44* (2006.01)
(52) U.S. Cl. ..................... 623/17.11; 604/27
(58) Field of Classification Search ................ 606/94, 606/90, 91, 92, 93, 95; 604/87, 89, 416, 604/26, 27; 128/898; 623/17.11
See application file for complete search history.

(56) References Cited

U.S. PATENT DOCUMENTS

| 3,889,665 | A |   | 6/1975  | Ling et al.        |         |
|-----------|---|---|---------|--------------------|---------|
| 4,294,251 | A | * | 10/1981 | Greenwald et al.   | 604/28  |
| 4,399,814 | A |   | 8/1983  | Pratt, Jr. et al.  |         |
| 4,466,435 | A |   | 8/1984  | Murray             |         |
| 4,627,434 | A |   | 12/1986 | Murray             |         |
| 4,941,872 | A | * | 7/1990  | Felix et al.       | 604/27  |
| 5,037,437 | A | * | 8/1991  | Matsen, III        | 128/898 |
| 5,108,404 | A |   | 4/1992  | Scholten et al.    |         |
| 5,395,317 | A | * | 3/1995  | Kambin             | 604/506 |
| 5,514,137 | A |   | 5/1996  | Coutts             |         |
| 5,520,667 | A | * | 5/1996  | Roche              | 604/290 |
| 5,554,111 | A |   | 9/1996  | Morrey et al.      |         |
| 5,558,646 | A |   | 9/1996  | Roche              |         |
| 6,149,655 | A | * | 11/2000 | Constantz et al.   | 606/94  |
| 6,348,055 | B1|   | 2/2002  | Preissman          |         |
| 6,558,390 | B2|   | 5/2003  | Cragg              |         |
| 7,008,433 | B2|   | 3/2006  | Voellmicke         |         |
| 2003/0032964 | A1 |   | 2/2003 | Watkins            |         |

OTHER PUBLICATIONS

Elmaraghy et al., The Role of Methylmethacrylate monomer in the formation and haemodynamic outcome Of pulmonary fat emboll; The Journal of Bone & Joint Surgery, vol. 80-B, No. 1; Jan. 1998, pp. 156-161.

Padovani et al. Pulmonary Embolism Caused by Acrylic Cement: A Rare Complication of Percutaneous Vertebroplasty; American Journal of Neuroradiology 20:375-377, Mar. 1999.

Amar et al, Percutaneous Transpedicular Polymethylmethacrylate vertebroplasty for the Treatment of Spinal Compression Fractures; Neurosurgery, vol. 49, No. 5, Nov. 2001.

(Continued)

*Primary Examiner*—Pedro Philogene

(57) ABSTRACT

This invention relates to improved vertebroplasty procedures for reducing embolisms, leakage and cement loosening.

9 Claims, 11 Drawing Sheets

OTHER PUBLICATIONS

Paradoxical Cerebral Arterial Emolization of Cement during intraoperative Vertebroplasty: Case Report, American Journal of Neuroradiology 23:868-870, May 2002.

Prophylaxis Against Fat and Bone-Marrow Embolism During Total Hip Arthroplasty Reduces the Incidence of Postoperative Deep-Vein Thrombosis, The Journal of Bone and Joint Surgery, vol. 84-A, Jan. 2002, pp. 39-48.

Miller, Daniel et al., Coaxial double-lumen methylmethacrylate reconstruction in the anterior cervical and upper thoracic spine after tumor resection, Journal of Neurosurgery: Spine, Apr. 2000, pp. 181-190, vol. 92.

Pitto et al., "Prophylaxis of Fat and Bone Marrow Embolism in Cemented Total Hip Arthroplasty", *Clinical Orthopaedics and Related Research*, 1998, pp. 23-24, No. 355, Lippincott Williams and Watkins.

Zioupos et al, "The Role of Collagen in the Declining Mechanical Properties of Aging Human Cortical Bone", *Collagen and The Fragility of Aging Bone*, 1999, pp. 108-116, John Wiley & Sons Inc.

Padovani et al. "Pulmonary Embolism Caused by Acrylic Cement: A Rare Complication of Percutaneous Vertebroplasty", *American Journal of Neuroradiology*, Mar. 1999, pp. 375-377. vol. 20.

Aebili et al., "Fat Embolism and Acute Hypotension During Vertebroplasty", *SPINE*, 2002, pp. 460-466, vol. 27, No. 5, Lippincott Williams & Wilkins Inc.

Affidavit of Alexandre DiNello dated Feb. 9, 2005.

* cited by examiner

METHODS OF PERFORMING EMBOLISM-FREE VERTEBROPLASTY AND DEVICES THEREFOR

CONTINUING DATA

This divisional patent application claims priority from U.S. Ser. No. 10/301,451, filed Nov. 21, 2002, now U.S. Pat. No. 6,979,352 entitled "Methods of Performing Embolism-Free Vertebroplasty and Devices Therefor" (Reynolds).

BACKGROUND OF THE INVENTION

In vertebroplasty, the surgeon seeks to treat a compression fracture of a vertebral body by injecting bone cement such as PMMA into the fracture site. In one clinical report, Jensen et al., *AJNR:* 18 Nov. 1997, Jensen describes mixing two PMMA precursor components (one powder and one liquid) in a dish to produce a viscous bone cement; filling 10 ml syringes with this cement, injecting it into smaller 1 ml syringes, and finally delivering the mixture into the desired area of the vertebral body through needles attached to the smaller syringes.

U.S. Pat. No. 6,348,055 ("Preissman") reports that the use of syringes to deliver bone cement in vertebroplasty procedures leads to high pressure spikes. Preissman discloses using a screw-type high pressure injection device to provide an even injection pressure during delivery of the bone cement.

Despite the relative success of vertebroplasty, there have been reports of complications such as embolisms. For example, Padovani, *Am. J. Neuroradiol.* 20: 375-377, March 1999, reports on a pulmonary embolus of acrylic cement found in a patient after percutaneous vertebroplasty, and suggests that the embolsim may have been caused by insufficient polymerizaion of the PMMA at the time of injection. Padovanni recommends adequate preparation of the bone cement and the use of biplane fluoroscopy as a means to lower the incidence of embolisms.

Amar, *Neurosurgery*, Vol. 49, No. 5, November 2001, also examined the issue of embolisms in vertebroplasty procedures and reports that some have suggested that needle placement near the geographic center of the vertebral body may increase the risk of pulmonary embolism or epidural compression, inasmuch as paravertebral and basivertebral veins frequently anastomose at that site.

Scroop, *Am. J. Neuroradiol.* 23:868-870, May 2002 provides a case report of a cerebral embolism during intraoperative vertebroplasty, and discusses both PMMA and fat embolisms. Scroop recommends that a maximum of three levels of vertebral bodies be treated in a single setting.

In sum, none of the art directed to vertebroplasty suggests removing fat or bone marrow prior to cement injection as a way of reducing embolisms.

U.S. Pat. No. 5,108,404 ("Scholten") discloses inserting an inflatable device within a passage within the vertebral body, inflating the balloon to compact the cancellous bone and create an enlarged void, and finally injecting bone cement into the void. Scholten further dicloses inserting an irrigation nozzle into the vertebral body after removing the balloon and irrigating the void with normal saline. See column 7, lines 36-40). Scholten further discloses injecting the bone cement through a double-barreled injection gun having a cement delivery tube and an aspirating tube that aspirates constantly. See column 7, lines 42-50).

Hip arthroplasty has long been concerned with pulmonary embolisms from fat and bone marrow. For example, U.S. Pat. No. 5,558,646 ("Roche") discloses that one conventional technique for managing the embolism problem is surgical lavage which include using an irrigating fluid to dislodge fat, marrow and debris, using suction to remove the dislodged soft tissue. Roche further suggests the use of hemostatic agents in such procedures. Pitto, *Clin. Orth. Rel. Res.* 355 (1998), pp. 23-34, discloses that the logical prophylactic measure to prevent intravasation of fat and bone marrow is to create sufficient drainage, and further suggests providing venting holes to reduce intramedullary pressure. However, none of the hip arthroplasty publications discussed above suggest that their techniques for lowering the incidence of embolisms should be applied to vertebroplasty.

Therefore, there is a need to improve the safety of the vertebroplasty, and in particular to reduce the frequency and severity of pulmonary embolism in vertebroplasty procedures.

SUMMARY OF THE INVENTION

The present inventor believes that the incidence of pulmonary embolism in vertebroplasty cases could be reduced by adopting at least one of the following measures:

First, the present inventor believes that the intravasation into vertebral veins of fat and bone marrow present in the soft tissue of the vertebral body may lead to embolism during vertebroplasty procedures. Now referring to FIG. 12, there is provided a cross section of a portion of the interior of a typical vertebral body comprising cancellous bone B and soft tissue ST. The present inventor believes that removing the source of the embolisms (i.e., the bone marrow and fat) from their residence within the interstices of the cancellous bone portion of the vertebral body prior to the injection of bone cement therein may help reduce the frequency and/or severity of pulmonary embolisms in vertebroplasty procedures.

Now referring to FIG. 1, there is provided a cross-section of a portion of the interior of the vertebral body vertebral body wherein the soft tissue portion has been removed, thereby removing a potential source of embolisms and creating a skeleton portion of bone B having open porosity P.

Therefore, in accordance with the present invention, there is provided a method of preparing a vertebral body having a porous cancellous bone structure having an open porosity and soft tissue contained therein, comprising the steps of:
a) removing at least a portion of the interstitial soft tissue from the cancellous bone structure to create a skeleton, and injecting bone paste into the skeleton.

In some embodiments, the removal of the soft tissue is accomplished in part by directing a fluid at the soft tissue to dislodge the soft tissue. Therefore, in accordance with the present invention, there is provided a method of preparing a vertebral body comprising a porous cancellous bone structure having open porosity and interstitial soft tissue contained therein, comprising the steps of:
a) directing a fluid into the open porosity of the porous cancellous bone structure to dislodge at least a portion of the soft tissue contained therein to create a skeleton, and
b) injecting bone paste into the skeleton.

Second, the present inventor believes that the presence of fat and bone marrow within the interstices of the cancellous bone portion of the vertebral body also reduces the effective pore size of the vertebral body, thereby requiring that higher pressures be used to adequately deliver bone cement into the vertebral body. FIG. 13 discloses the injection of cement C into a typical vertebral body essentially filled with soft tissue ST and cancellous bone B. The essentially dense nature of this cross-section is the reason why high pressure injection is are required, as the cement must force its way into the structure and in doing so must displace the local fat and bone marrow. These higher pressures may facilitate the intravasation of bone marrow and fat into the vertebral veins. Accordingly, the present inventor believes that removing the bone marrow and fat from the interstices of the cancellous bone portion of the vertebral body may help increase the effective pore size of the vertebral body, and thereby reduce the pressure needed to adequately deliver bone cement into the vertebral body.

Now referring to FIG. 2, there is provided a cross-section of a skeletonized portion of a vertebral body having a bone portion B having open porosity P, wherein bone paste BP is being injected through a cannula. The large effective pore size of the skeleton allows easy injection of the cement under lower pressure.

Therefore, in accordance with the present invention, there is provided method of preparing a vertebral body having a porous cancellous bone structure having a natural effective pore size, comprising the steps of:
  a) increasing the effective pore size of at least a portion of the porous cancellous bone structure to create a portion having an augmented pore size, and
  b) injecting bone paste into the portion having the augmented pore size.

Third, the present inventor further believes that high pressures associated with conventional vertebroplasty procedures may be due in part to the essentially closed nature of the vertebral body. That is, even when cement is injected into a volume having significant open porosity, the cement nonetheless reduces the porosity of the volume, so that the last increments of cement that fill that volume may need to be injected under high pressure. Accordingly, the present inventor believes that a pressure relief means may also be used as a way of relieving pressure built up by a cement injection. One particular pressure relief means comprises a second passageway extending from the outside of the vertebral body to the skeleton. FIG. 3 discloses a cross section of a vertebral body having a first passageway P, a skeleton portion SK, and a second passageway P2. This second passageway provides the cement with a low pressure route for relieving the excess pressure produced by the filling that could exacerbate embolisms.

Therefore, in accordance with the present invention, there is provided a method of preparing a vertebral body having a porous cancellous bone structure having bone marrow and fat therein, comprising the steps of:
  a) forming a first passage in a vertebral body,
  b) forming a second passage in a vertebral body,
  c) injecting bone paste into the first passage, and
  d) flowing the paste from the first passage into the second passage.

Fourth, the present inventor has also noted that, in conventional cases involving embolisms, fat and marrow may enter the circulatory system through veins injured either during the placement of needles and cannulae in the vertebral body, or prior to the invasive procedure (such as during a compression fracture). The present inventor believes that occluding the vertebral body veins injured during needle access may reduce the frequency of fat or marrow embolisms in vertebroplasty.

Therefore, in accordance with the present invention, there is provided a method of preparing a vertebral body having a porous cancellous bone structure having an open porosity and soft tissue contained therein, comprising the steps of:
a) creating a passage within the porous cancellous bone structure to produce an injured vein therein having an opening, and
b) thermally treating the injured vein to occlude the opening.

Also in accordance with the present invention, there is provided a method of preparing a vertebral body having a porous cancellous bone structure having an open porosity and soft tissue contained therein, comprising the steps of:
a) creating a passage within the porous cancellous bone structure to produce an injured vein therein having an opening, and
b) contacting the injured vein with a hemostat to clot the opening.

Further, the present inventor believes that the measures described above that either reduce the pressure of the injected cement within the vertebral body or occlude veins may further reduce the likelihood of cement intravasation into the veins as well, thereby reducing the likelihood of cement emboli as well.

The present inventor believes that the incidence of uncontrolled leakage in vertebroplasty cases could be reduced by adopting some of the following control measures:

First, the present inventor believes that the measures discussed above for reducing intra-vertebral pressure induced by cement injection (i.e., increasing the effective pore size of the vertebral body and providing a relief passage) may also reduce the incidence of uncontrolled leakage in vertebroplasty. That is, the present inventor believes that the methods described above may also provide controlled paths of least resistance for the cement injected into the vertebral body. In particular, a larger effective pore size may reduce the pressure increase in the vertebral body associated with a given volume of cement, and thereby reduce the incidence of leakage caused by the cement preferentially passing through fracture planes or other planes of egress from the vertebral body. The extra volume associated with the increased pore size may also act as a path of least resistance for the cement as well. Likewise, providing a relief passage may guide overpressurized cement present within the skeleton in a predetermined direction and not into fracture planes or other planes of egress from the vertebral body.

FIGS. 4a-4f provide a more detailed description of the advantage provided by the larger effective pore size is reducing uncontrolled leakage. FIG. 4a discloses a cross-section of an interior portion of a vertebral body prior to application of the present invention including a crack CR, interconnected bone B, and soft tissue ST (characterized by orthogonal lines). In FIG. 4b, a portion of the soft tissue region of the vertebral body is removed (by process disclosed below). FIG. 4c discloses the continued removal of the soft tissue and the consequent creation of a skeleton portion SK within the vertebral body. FIG. 4d discloses a skeleton portion completely traversing the cross section. FIG. 4e discloses the introduction of bone paste BP into the skeleton from the lower half of the FIG. FIG. 4f discloses the bypassing of the crack CR by the cement. The bypass occurs because the large effective pore size created by the skeleton offers the cement a path of resistance that is lower than that of the crack CR.

In addition, the second passage can be used in conjunction with a vacuum source as a means to provide superior infiltration of the cement into the skeleton. In conventional vertebroplasty systems, the cement is ejected from a cannula opening and control of the cement is lost once the cement has left the cannula. This lack of control of ejected cement may lead to uncontrolled leakage or to ineffective filling. In embodiments of the present invention having a second passageway, suction can be provided at the second passage in an amount sufficient to direct the bone cement through the skeleton. This has the advantage of insuring that the cement substantially flows into the desired porous volume. Moreover, the danger of leakage in undesired directions is reduced because the practitioner still retains a measure of control over the cement even after the cement has entered the vertebral body. In particular, cement within the skeleton will be directed into the relief passage and not into an undiscovered crack. This concept of "directed flow" appears to be completely novel to vertebroplasty.

Therefore, in accordance with the present invention, there is provided a method of preparing a vertebral body comprising a porous cancellous bone structure having open porosity and interstitial soft tissue contained therein, comprising the steps of:
a) applying suction to the porous cancellous bone structure to remove the soft tissue contained therein.

Also in accordance with the present invention, there is provided a method of preparing a vertebral body having a porous cancellous bone structure having open porosity and soft tissue contained therein, comprising the steps of:
a) forming a first passage in the vertebral body,
b) injecting bone paste into the first passage,
c) applying suction to the vertebral body in an amount sufficient to cause the bone paste to infiltrate the porosity of the vertebral body.

Lastly, the present inventor believes that the incidence of cement loosening in vertebroplasty cases could be reduced by adopting some of the following control measures:

First, the present inventor believes that the measures discussed above for reducing pressure (i.e., increasing the effective pore size of the vertebral body and providing a relief passage) may also be effective in reducing the incidence of cement loosening in vertebroplasty. In particular, since the skeletonized portion of the vertebral body is still well connected to the remainder of the vertebral body, injecting cement into the skeletonized portion of the vertebral body will provide excellent interdigitation between the cement and the cancellous bone of the skeleton (thereby increasing adhesion strength). Moreover, directing the cement into a second passage will provide a gross anchor (or keel) for the interdigitated cement present within the skeleton.

In addition, the present inventor has also noted that, in conventional vertebroplasty cases, blood likely enters the vertebral body through arteries injured during the placement of needles and cannulae in the vertebral body or otherwise. This blood may intermix with the uncured cement and reduce its strength. Moreover, since this blood enters the vertebral body under pressure, its pressurized entry may allow blood to interpose itself between bone and cement at the cement-bone interface, and thereby prevent sufficient bonding therebetween. The present inventor believes that occluding the vertebral body arteries injured during needle access or otherwise may reduce the presence of blood within the vertebral body, and so reduce the frequency of cement loosening in vertebroplasty.

Therefore, in accordance with the present invention, there is provided a method of preparing a vertebral body having a porous cancellous bone structure having an open porosity and soft tissue contained therein, comprising the steps of:
a) creating a passage within the porous cancellous bone structure to produce an injured artery therein having an opening, and
b) thermally treating the injured artery to occlude the opening.

Also in accordance with the present invention, there is provided a method of preparing a vertebral body having a porous cancellous bone structure having an open porosity and soft tissue contained therein, comprising the steps of:

a) creating a passage within the porous cancellous bone structure to produce an injured artery therein having an opening, and
b) contacting the injured artery with a hemostat to clot the opening.

In addition, as the present inventor believes that providing a dry bone-cement interface will increase the bonding between the bone and cement, the present inventors believe that removing any blood (from injured arteries) or saline (from irrigation) from the bone surface will produce the dry bone surface needed for good cement-bone bonding.

Therefore, in accordance with the present invention, there is provided a method of preparing a vertebral body having a porous cancellous bone structure having bone marrow and fat therein, comprising the steps of:
a) directing a fluid into the porous cancellous bone structure to remove the soft tissue from the cancellous bone and produce an open porosity, and
b) applying suction to the open porosity to dry the skeleton portion.

DETAILED DESCRIPTION OF THE INVENTION

For the purposes of the present invention, the term "soft tissue" includes bone marrow and fat; the term "skeleton" refers to the intact cancellous bone structure having open porosity; the term "debris" refers to soft tissue that has been dislodged from the cancellous bone portion of the vertebral body. Loose bone chips may also be associated with the debris.

When the practitioner desires to prepare the cancellous bone in a manner that will allow good interdigitation of the bone cement, a portion of the cancellous bone region is preferably copiously irrigated (preferably by lavage, more preferably by a pulsed lavage) to dislodge the soft tissue, and then suctioned to remove debris. The resulting structure is a skeleton of cancellous bone from whose interstices the intercancellous marrow, fat and other fluids have been removed to create an open porosity. The skeleton structure allows a deeper and more uniform interdigitation of the cement within the bony structure, thereby creating a more secure cement to bone construct.

In one preferred procedure, bilateral access to the vertebral body is created, either transpedicularly or extrapedicularly, by a pair or appropriately sized cannulae. Suction is then applied to the distal opening of a first cannula followed by the introduction of a flushing liquid like isotonic saline from the distal opening of the second cannula. The combination of flushing and suction can sufficiently dislodge enough soft tissue in the cancellous bone portion to create a flow pattern within the cancellous bone portion of the vertebral body that safely flushes out the fat and marrow of the soft tissue within the cancellous structure. In some preferred embodiments, flushing is considered complete when the liquid exiting the suction cannula appears clear. In some embodiments, flow can then be stopped. In other embodiments, a second flush with a hemostat (such as concentrated fibrinoigen) may be introduced through the second cannula in order to reduce or eliminate bleeding. In some embodiments, a third flush with saline is made in order to remove any excess hemostat.

In preferred embodiments, additional suction is applied after flushing has ceased in order to evacuate the skeleton portion of any excess liquid (e.g., blood, saline or hemostat), thereby leaving a dried cancellous skeleton capable of being easily infiltrated by bone cement.

Figure 1:
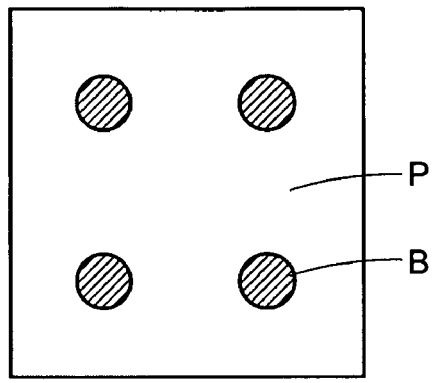
FIG. 1 discloses a cross-section of a portion of a vertebral body prepared according to an embodiment of the present invention, wherein the soft tissue therein has been removed to create a skeleton of cancellous bone B and porosity P.
Figure 2:
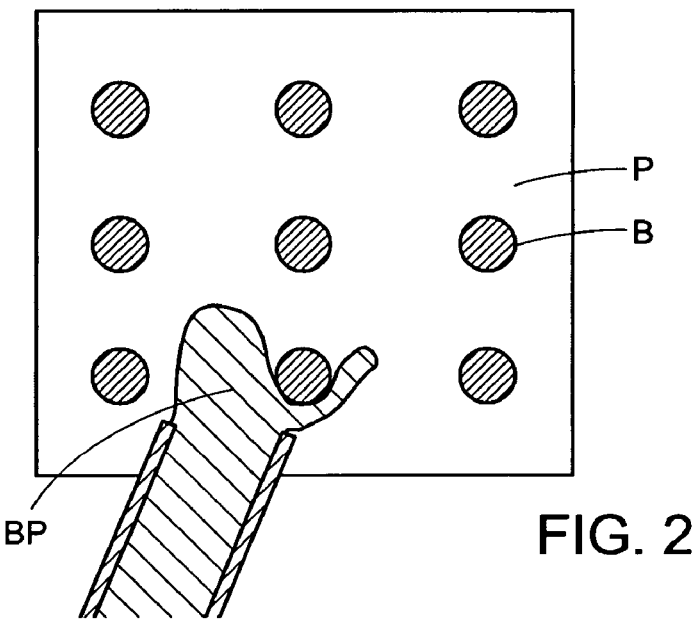
FIG. 2 discloses a procedure according to the present invention comprising the step of filling the skeletonized portion of the vertebral body with a bone paste BP.
Figure 3:
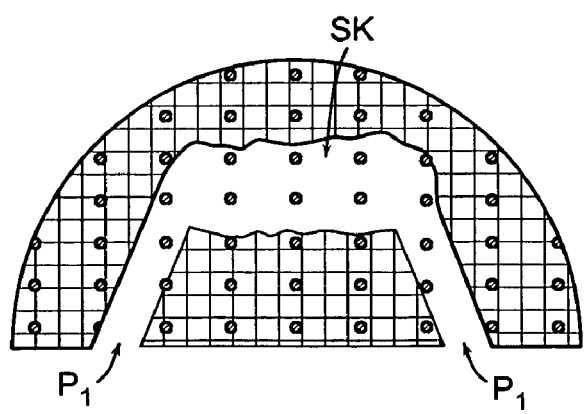
FIG. 3 discloses a cross-section of a vertebral body prepared according to an embodiment of the present invention, wherein a second pasageway in connection with the skeleton is provided.
Figure 4A:
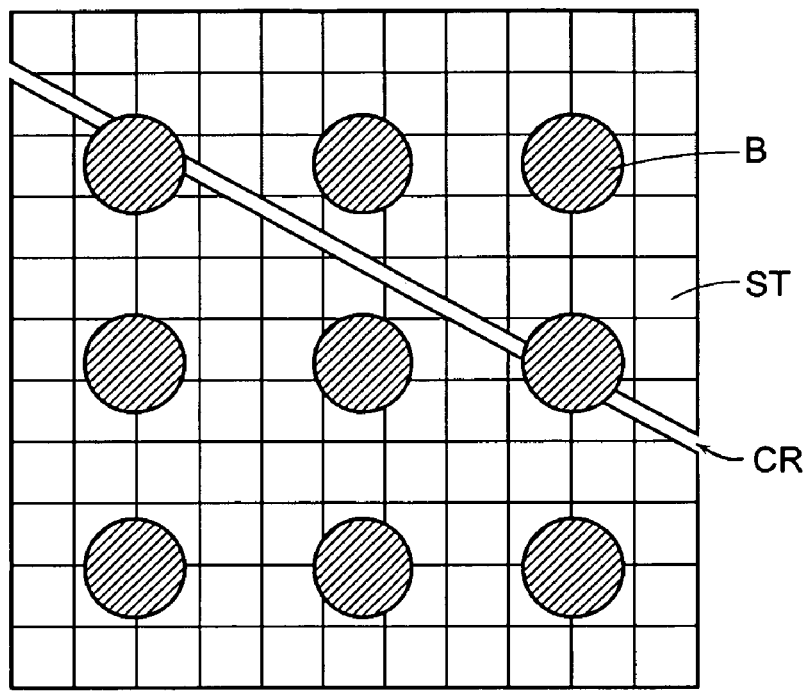
FIGS. 4a-4f disclose a sequential cross-sections of a portion of a vertebral body prepared according to an embodiment of the present invention.
Figure 4B:
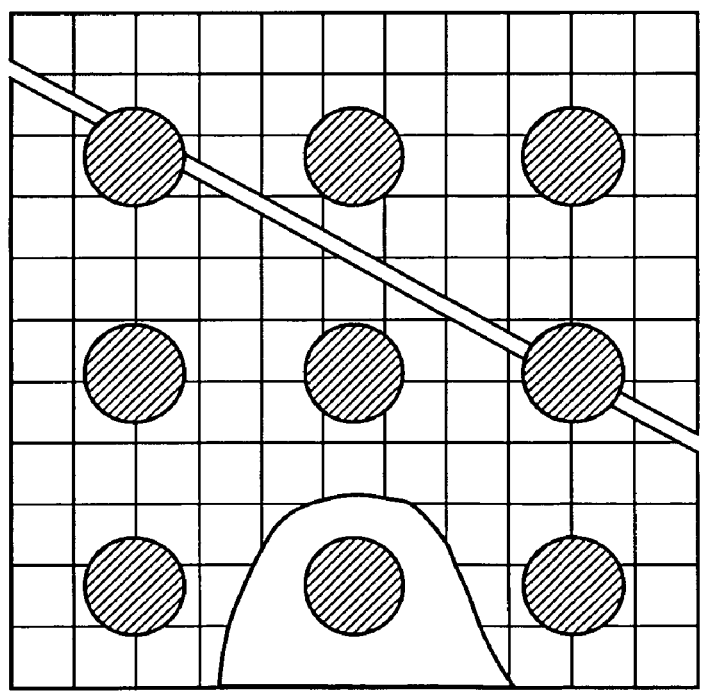
Figure 4C:
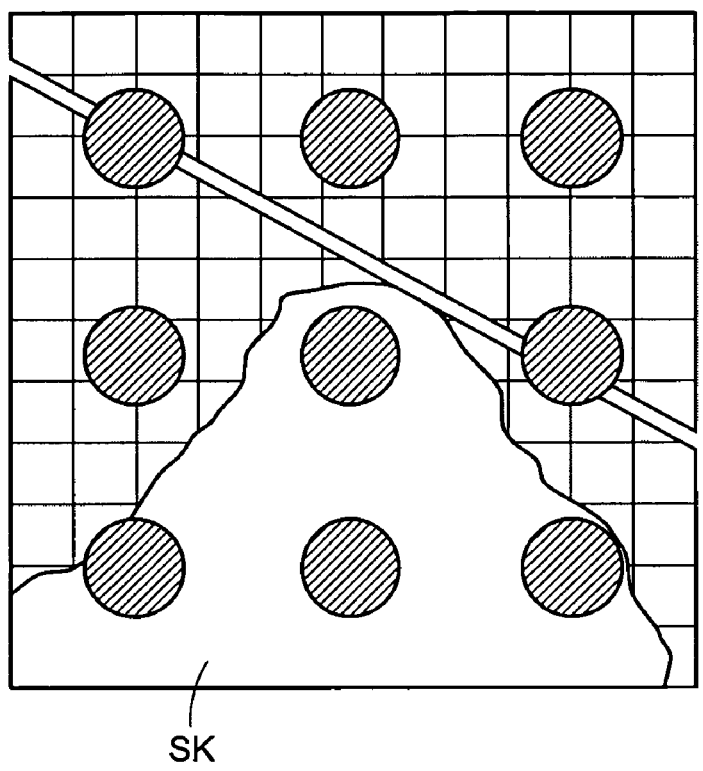
Figure 4D:
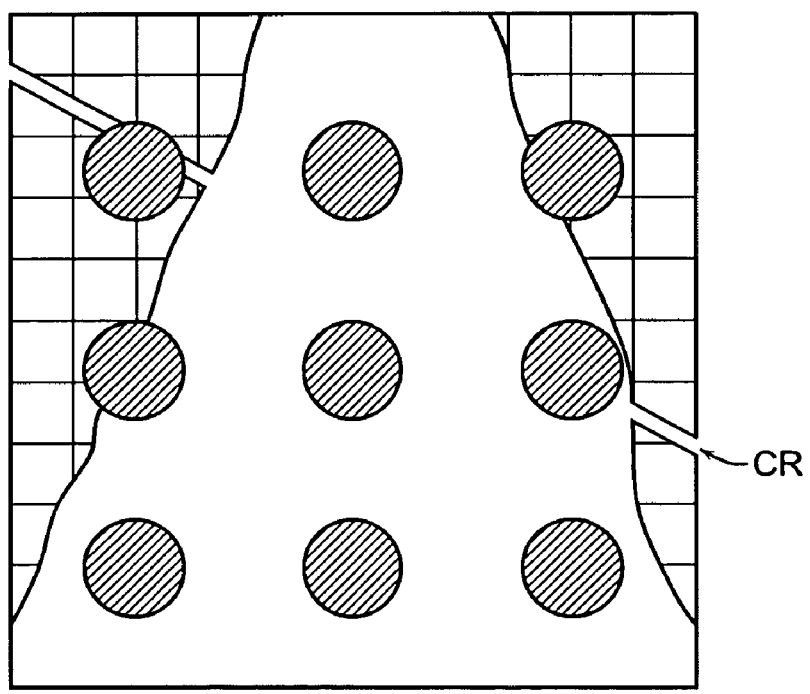
Figure 4E:
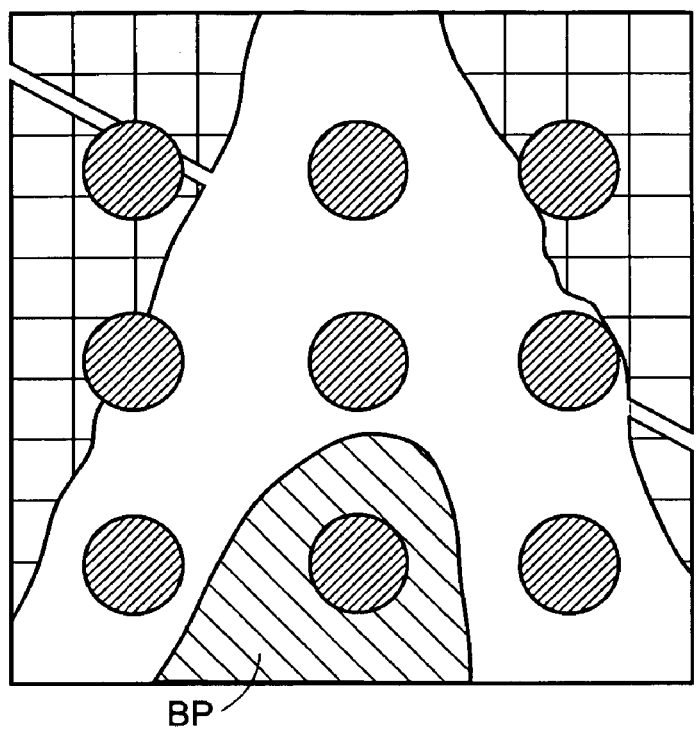
Figure 4F:
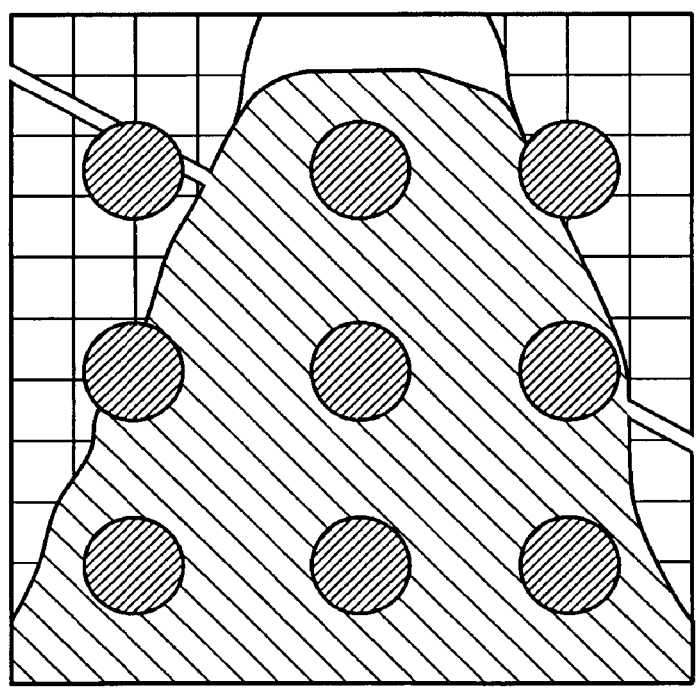
Figure 5A:
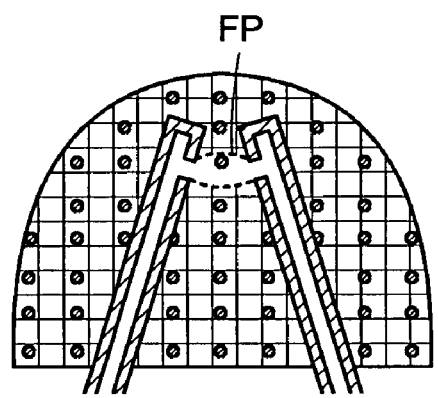
FIGS. 5a-5c disclose cross-sections of various placements of cannulae within a vertebral body in accordance with embodiments of the present invention FIG. 6 discloses cross-sections of a cannlua and a stylet used in embodiments of the present invention.

The size, shape and location of the skeleton produced by this procedure can be influenced by varying the relative locations of the irrigation and suction cannulae. For example, and now referring to FIG. 5a, in one embodiment, each cannula is placed trans-pedicularly and is located deep in the vertebral body (i.e., on the anterior half) to yield a substantially lateral flow path FP. This flow path will create a cancellous skeleton having a volume substantially the same as the flow path, thereby providing a preferential path far away from the posterior portion of the vertebral body.

Figure 5B:
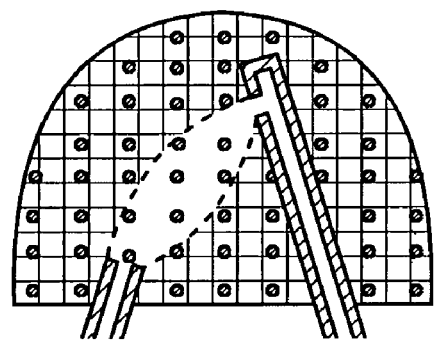

Now referring to FIG. 5b, in one embodiment, the irrigation cannula IC is placed transpedicularly and is advanced only a minimal amount into the vertebral body (i.e., opens on the posterior half of the body), while the suction cannula SC is placed transpedicularly and advanced as far anteriorly as possible to yield an angled posterior-to-anterior flow path. This flow path will create a cancellous skeleton having a volume substantially the same as the flow path, thereby providing a preferential path away from the posterior portion of the vertebral body.

Figure 5C:
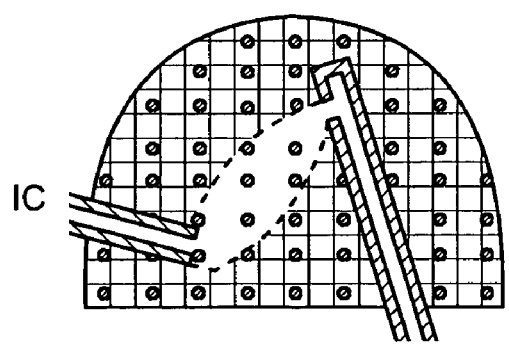

Now referring to FIG. 5c, in one embodiment, the irrigation cannula is placed extra-pedicularly and is advanced only a minimal amount into the vertebral body, while the suction cannula is placed transpedicularly and advanced as far anteriorly as possible to yield a substantially posterior-to-anterior flow path. This flow path will create a cancellous skeleton having a volume substantially the same as the flow path, thereby providing a preferential path directly away from the posterior portion of the vertebral body.

In some embodiments, the flow can be further fanned out by adding a series of longitudinally-spaced suction holes to the suction cannula.

The advantages provided by these embodiments of the present invention include but are not limited to, the following:
a) the development of a porous cancellous skeleton allows easy infiltration of bone cement by a low pressure injection, thereby avoiding the need for a high pressure injection and the crushing of the cancellous structure which may undesirably force bone marrow, fat or cement intravasation into the veins;
b) the development of a porous cancellous skeleton allows easy infiltration of bone cement by a low pressure injection, thereby avoiding the need for a high pressure injection and the decreasing the risk of cement extravasation;
c) the development of a porous cancellous skeleton provides the opportunity to introduce a hemostatic agent to the structure to seal veins, and thereby arrest the possibility of fat, marrow or cement intravasation into veins; and
d) the interdigitation of the cement into the porous cancellous skeleton could provide a better mechanical result by preserving the integrity of the skeleton, leading to a composite or reinforced mechanical structure.

In some embodiments, the present invention includes a device for creating a passageway into and through the vertebral body. This passageway provides access to cancellous bone portion of the vertebral body. Typically, since the cortical bone shell of the vertebral body is typically much harder than the cancellous bone portion, this device includes a means for penetrating the cortical bone portion of the vertebral body, and is typically a sharpened distal tip.

In some embodiments, this device comprises a stylet. Typically, the stylet is introduced through a percutaneuous cannula, bores a hole through the outer cortical bone and proceeds to bore a tubular-shaped void in at least a portion of the cancellous bone portion as well. Now referring to FIG. 6, stylet 201 comprises a shaft 203 having a longitudinal axis "A", and a proximal 205 and distal end 207. Disposed at the distal end of the shaft is a sharpened tip 209 adapted for boring or drilling through bone. The outer diameter $D_O$ of the shaft is adapted to be received within the inner diameter of the cannula.

In other embodiment, a rotary cutting device such as a drill may be used as the device for creating a passageway into the vertebral body. In other embodiments, an obdurator may be used. In other embodiments, a chisel may be used.

In some embodiments, the present invention includes a device for providing a working portal for the devices and fluids introduced into the vertebral body. In some embodiments, this device is a cannula.

Figure 6:
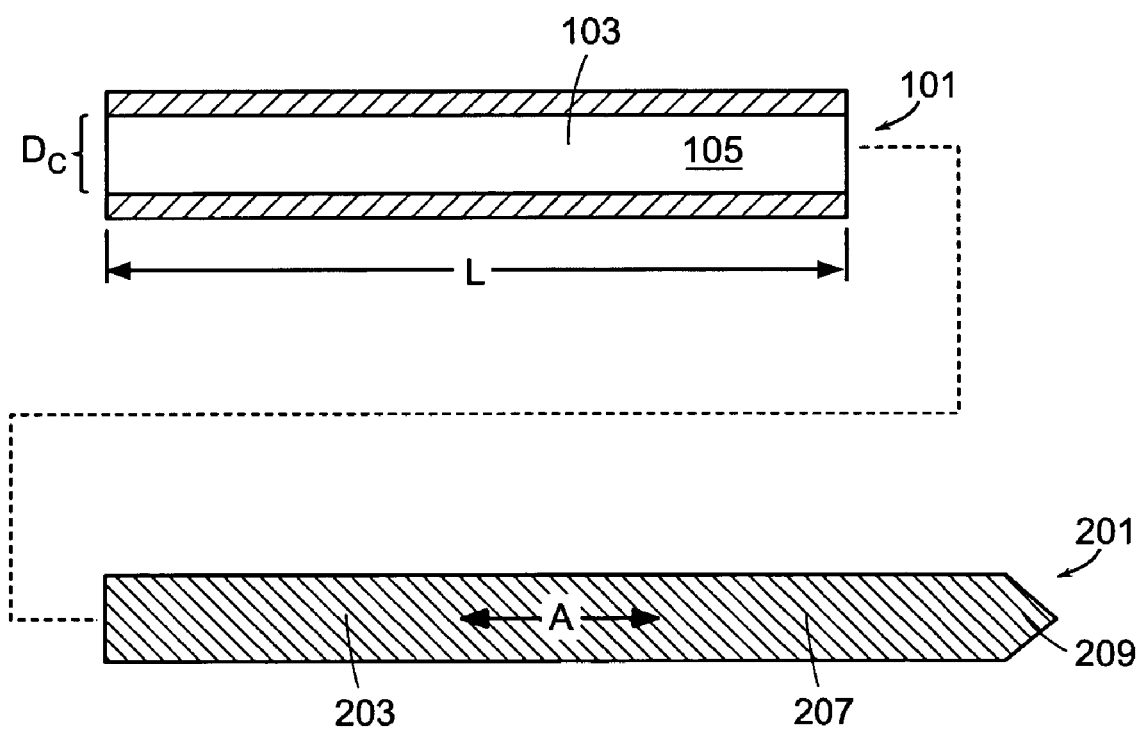

Now referring to FIG. 6, cannula 101 comprises a shaft 103 having a longitudinal bore 105 therethrough defining an inner diameter $D_C$. The cannula provides a working portal for other devices and fluids used in the present invention. The length of the cannula is sized to reach from the patient's skin (proximally) to the interior portion of the vertebral body.

Now referring to FIG. 6, there is provided a preferred combined device for creating both the precutaneous passageway and the passageway in the bone. According to the present invention, this combination comprises first cannula 101 and first stylet 201. For simplicity, only a single cannula and stylet will be further described. However, the skilled artisan will appreciate that preferred embodiments may use two sets of such devices. For the purposes of the present invention, the combination of the cannula and the stylet is referred to as a "cannulated needle". In some embodiments, access to the vertebral body is gained by first placing the stylet in the cannula to produce the cannulated needle, piercing the skin with the cannulated needle, and advancing the cannulated needle so that the stylet tip reaches the mid-portion of the vertebral body, and then withdrawing the stylet. This procedure produces a cannula conveniently located to receive the devices of the present invention.

In some embodiments, the present invention includes a device for removing soft tissue from the open porosity of the vertebral body.

In many embodiments thereof, this device comprises a pressure source adapted for introducing an impaction fluid into the vertebral body at a high velocity. The momentum produced by the velocity and mass of the impaction fluid creates an impaction force upon the soft tissue sufficient to dislodge the soft tissue from the skeleton.

Figure 7A:
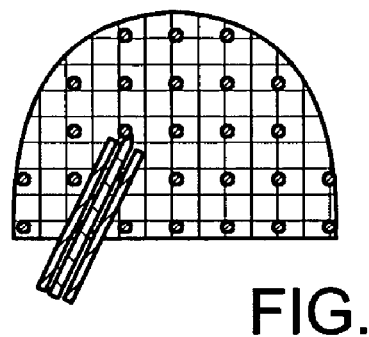
FIGS. 7a-c disclose cross-sections of an embodiment of the present invention, wherein a bulb is used as a device for dislodging soft tissue from the cancellous bone portion.
Figure 7B:
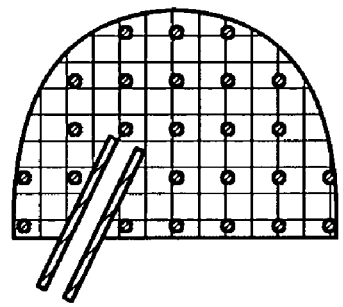
Figure 7C:
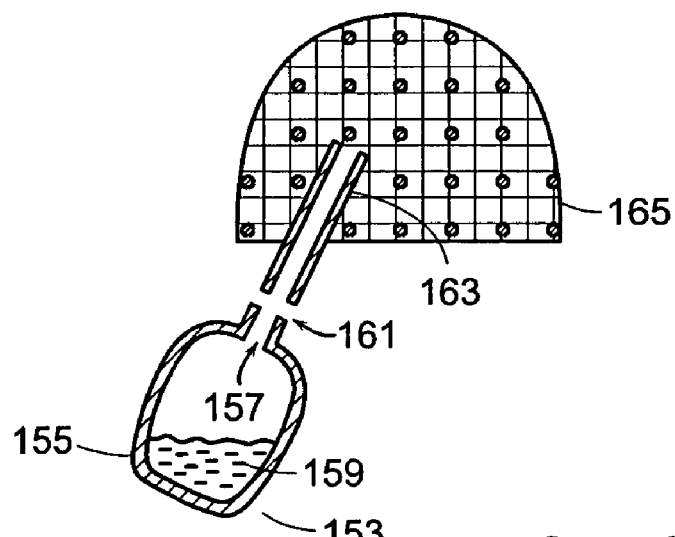

Now referring to FIGS. 7a-c, in some embodiments, this device comprises a bulb 153 comprising a flexible container portion 155 and an exit port 157. In preferred embodiments, the bulb is filled with a lavage fluid 159 and the exit port is attached to the proximal opening 161 of a working cannula 163 by, for example a luer connection (not shown). Pressurization of the bulb (for example, by squeezing the flexible container portion) forces the lavage fluid out of the container and through the exit port and into the cannula and into the vertebral body 165. The momentum of the lavage fluid is such that its impact upon the soft tissue causes dislodgement of the soft tissue from the skeleton.

In some embodiments, the bulb may also be used as a device for removing the debris from the vertebral body.

Figure 8:
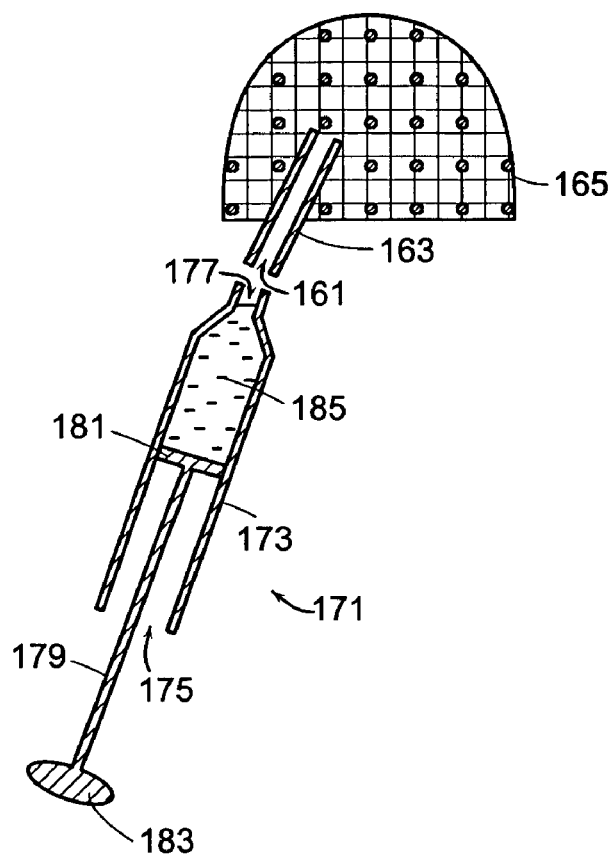
FIG. 8 discloses a cross-section of an embodiment of the present invention, wherein a syringe is used as a device for dislodging soft tissue from the cancellous bone portion.

In some embodiments, this device comprises a syringe. Typically, and now referring to FIG. 8, the syringe 171 comprises a barrel 173 having a first relatively wide proximal opening 175 and a second relatively narrow distal opening 177, and a plunger 179 having a piston 181 adapted to create a movable, substantially fluid tight seal of the first opening and a handle 183 proximally attached to the piston. In preferred embodiments, the syringe is first filled with a lavage fluid 185. This may be accomplished by placing the second opening in a container containing the lavage fluid and proximally moving the piston, thereby creating a vacuum in the barrel and drawing lavage fluid therein. Next, the exit port of the syringe is attached to the proximal opening 161 of a working cannula 163 disposed within the vertebral body 165. Next, the piston is advanced distally to force the lavage fluid out of the barrel and through the second opening, through the cannula and into the vertebral body. The momentum of the impaction fluid produced by the advance of the piston is such that its impact upon the soft tissue creates a force sufficient to dislodge of the soft tissue from the cancellous bone portion of the vertebral body.

In some embodiments, the syringe may also be used as a device for removing the debris from the vertebral body. In these embodiments, once debris has been created within the vertebral body, a syringe with a distally disposed piston 181 is attached to the proximal end of a working cannula, and the piston is moved proximally to create a vacuum in the barrel and draw soft tissue debris thereinto.

Figure 9:
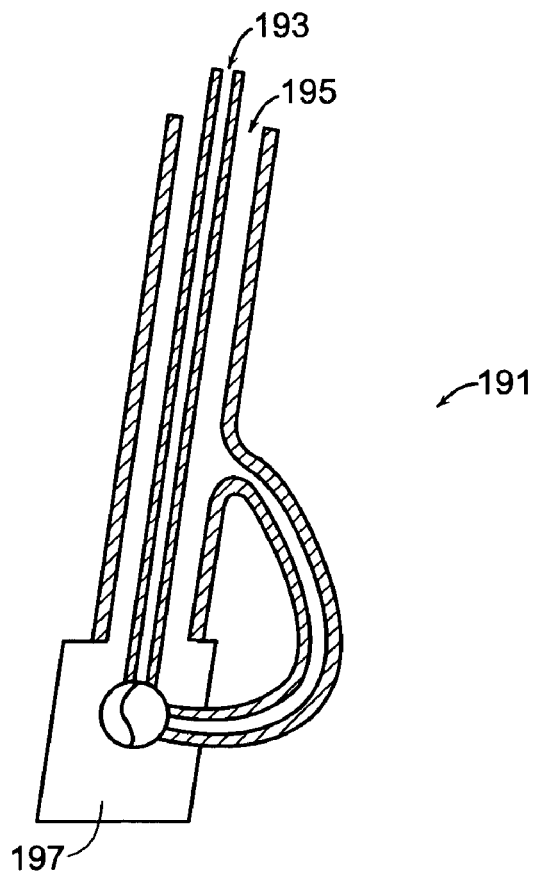
FIG. 9 discloses a cross-section of a device for removing soft tissue from the open porosity of the vertebral body that is capable of providing a continuous flow.

In some embodiments, the device for removing soft tissue from the open porosity of the vertebral body is capable of providing a continuous flow. Preferably, and now referring to FIG. 9, such a device 191 comprises a fluid exit port 193, a fluid entry port 195, and a pump 197 in fluid connection with each port. The pump allows the impaction fluid to continuously impact the soft tissue, thereby providing a lavage.

In some embodiments, the device for removing soft tissue from the open porosity of the vertebral body is capable of providing a pulsed, quasi-continuous flow.

In some embodiments, the removal of soft tissue from the open porosity of the vertebral body is accomplished by introducing an impaction fluid into the vertebral body. The momentum of the impaction fluid is such that its impact upon the soft tissue creates a force sufficient to dislodge of the soft tissue from the skeleton.

In preferred embodiments, the impaction fluid is bioresorbable. In this condition, its leakage from the vertebral body need not be of any concern. Preferably, the impaction is aqueous-based. More preferably, the impaction fluid consists essentially of water. In preferred embodiments, comprises electrolytes, preferably in concentrations approximating human plasma. More preferably, the impaction fluid comprises saline, preferably isotonic saline.

It is understood that the basivertebral nerve ("BVN") located within the vertebral body may be associated with back pain, and that denervation of the BVN may provide relief for the patient. It is further understood that nerves such as the BVN are denervated at temperatures as low as 42° C. Therefore, in some embodiments, the impaction fluid has a temperature of at least 42° C., preferably at least 50° C., more preferably at least 60° C. When the tissue surrounding the BVN experiences a temperature above 42° C., nerves within the target tissue may be desirably damaged. However, it is believed that denervation is a function of the total quantum of energy delivered to the target tissue, i.e., both exposure temperature and exposure time determine the total dose of energy delivered. Accordingly, if the temperature of the target tissue reaches only about 42° C., then it is believed that the exposure time of the volume of target tissue to that temperature should be at least about 30 minutes and preferably at least 60 minutes in order to deliver the dose of energy believed necessary to denervate the nerves within the target tissue. Preferably, it is desirable to heat the volume of target tissue to a minimum temperature of at least 50° C. If the temperature of the target tissue reaches about 50° C., then it is believed that the exposure time of the volume of target tissue to that temperature need only be in the range of about 2 minutes to 10 minutes to achieve denervation. More preferably, it is desirable to heat the volume of target tissue to a minimum temperature of at least 60° C. If the temperature of the target tissue reaches about 60° C., then it is believed that the exposure time of the volume of target tissue to that temperature need only be in the range of about 0.1 minutes to 1.5 minutes to achieve denervation, preferably between 0.1 and 0.25 minutes.

Preferably, the impaction fluid has a low viscosity so that it may flow easily. In this condition, it can be easily introduced at a high velocity that produces a large momentum.

In many embodiments thereof, the device for removing soft tissue from the open porosity of the vertebral body comprises an ablation source adapted for ablating the soft tissue. The ablation source may vaporize or necrotize the soft tissue, thereby at least partially dislodging the soft tissue from the cancellous bone, while leaving cancellous bone relatively unharmed. In preferred embodiments, the ablation source comprises a Rf energy-transmitting device, preferably having an active and return electrode.

In some embodiments, the ablation of soft tissue is accomplished by introducing an electroconductive fluid into the vertebral body. This fluid helps create an electrical pathway between the active and return electrodes of an ablation source. In preferred embodiments, the electroconductive fluid has an electroconductivity greater than that of isotonic saline (i.e, is hyperconductive). More preferably, the hyperconductive fluid comprises saline having a NaCl concentration of between 10% and 35%.

In many embodiments thereof, the device for removing soft tissue from the open porosity of the vertebral body comprises a digestion source adapted for in-situ digesting of the soft tissue. The digestion source may biologically, thermally or chemically break down the soft tissue, thereby at least partially dislodging the soft tissue from the cancellous bone, while leaving cancellous bone relatively unharmed. In preferred embodiments, the digestion source comprises a digestion fluid-transmitting device (such as a cannula), preferably further comprises a pressure source for flowing the digestion fluid (such as a pump).

In some embodiments, the digestion of soft tissue is accomplished by introducing a digestion fluid into the vertebral body. The digestion source may include biological, thermal and/or chemical means to break down the soft tissue. In some embodiments, the digestion source comprises cells adapted to biologically digest the soft tissue. In some embodiments, the digestion source comprises a heated fluid adapted to thermally break down the soft tissue. In some embodiments, the digestion source comprises a chemical reactant adapted to chemically break down the soft tissue. Such chemical reactants may include hydrogen peroxide.

It has been noted that the introduction of the stylet or drill into the cancellous bone portion of the vertebral body creates damage to the cancellous bone and exposes veins. These exposed veins may provide the conduits fat or bone marrow to be introduced into the circulatory system.

Therefore, in some embodiments, the present invention includes a device for coagulating veins injured during the creation of the passageway.

In some embodiments, this device is thermally-based. In some embodiments, this device may simply provide a heated surface adapted to contact the tissue surrounding the injured veins, such as a resistive heating element. Heat is conducted from the heated surface into this tissue, thereby heating the tissue and welding/coagulating the injured veins. In other embodiments, this device may be an energy transmitting device that transmits energy into the injured region and heats the injured region to a temperature sufficient to weld or coagulate the injured veins. Preferably, the energy transmitting device has an active electrode and a return electrode.

In other embodiments, this device for coagulating veins is fibrinogen-based. In some embodiments, this fibrinogen-based device delivers fibrinogen to the tissue surrounding the injured veins, thereby clotting the injured veins. More preferably, the device further delivers thrombin, preferably in an amount sufficient to accelerate the clotting process. In some embodiments, the device may be a simple syringe (preferably containing fibrinogen) that is attached to a cannula whose distal opening opens upon the skeleton.

It has been further noted that the introduction of the stylet or drill into the cancellous bone portion of the vertebral body creates damage to the cancellous bone and severs arteries therein. These severed arteries cause blood to enter the passageway. This blood may interpose itself between the skeleton and the bone cement, and thereby inhibit the effectiveness of the interdigitation between the skeleton and the bone cement.

Therefore, in some embodiments, the present invention includes a device for coagulating arteries severed during the creation of the passageway. Preferably, the devices used for coagulating veins injured during the creation of the passageway are used for coagulating severed arteries as well, preferably simultaneuously.

In some embodiments, the present invention includes a device for removing the soft tissue debris dislodged from the open porosity of the vertebral body. Removal of the debris desirably reduces the possibility that debris may enter the vertebral veins and cause an embolism. In addition, removal of the debris increases the effective porosity of the cancellous bone portion of the vertebral body, so that subsequent injection of bone cement into the skeleton can be performed under a relatively lower pressure.

In preferred embodiments, the device for removing the soft tissue debris comprises a suction source. When suction is applied to the debris, the suction pulls the debris out of the vertebral body, thereby leaving a skeleton suitable for safe low pressure filling by bone cement.

In preferred embodiments, the suction source comprises an aspirator. In some embodiments, the suction source may comprise the bulb or syringe used to deliver the lavage fluid.

In other embodiments, the device for removing the soft tissue debris comprises a high pressure source. When high pressure is applied to the debris, the high pressure forces the debris out of the vertebral body, thereby leaving a skeleton suitable for safe low pressure filling by bone cement.

In some embodiments, the pressure source is selected from the group consisting of a syringe and a bulb.

In some embodiments including a device for removing the soft tissue debris, an exit passageway is created in the cancellous bone to facilitate the removal of the debris. In these embodiments, a pathway is created comprising the entrance passage, the skeleton, and the exit passage. The pathway allows a pressure source to used from one of the passages and a suction source to be used from the remaining passage to facilitate debris removal. In some embodiments, the pressure source and suction source are used simultaneously. In some embodiments, the pressure source and suction source are providing by at least one pump, and preferably a single pump.

In some embodiments, the present invention includes a debris collection container for collecting the soft tissue debris removed from the vertebral body.

In preferred embodiments, the debris collection container comprises a container having an entry port. This entry port is preferably in fluid connection with the exit passage from which debris exits the vertebral body.

Figure 10:
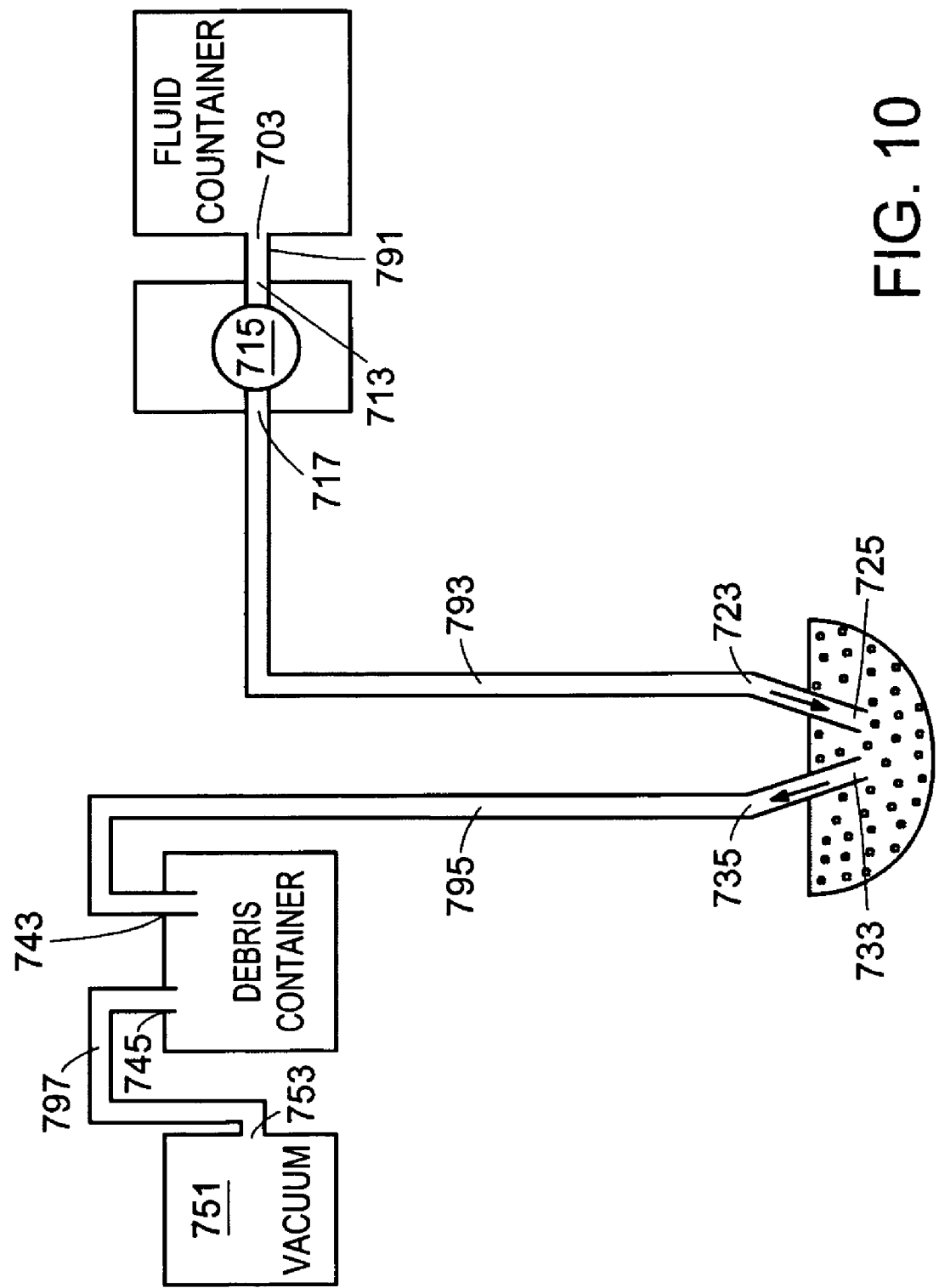
FIG. 10 discloses a cross-section of a preferred apparatus of the present invention in use.

Now referring to FIG. 10, in one preferred embodiment, the apparatus comprises:
a) a lavage container 701 for holding the lavage fluid;
b) a pump 711 for pressurizing the lavage fluid,
c) an entry cannula 721 for delivering the lavage fluid to the cancellous bone portion to be skeletonized,
d) an exit cannula 731 for removing the debris produced by the lavage,
e) a debris container 741 for collecting the debris, and
f) a suction source 751 for assisting the removal and collection of the debris.

The lavage container further has an opening 703 in fluid connection with a proximal opening 713 in pump 711 via tube 791. The pump further comprises a pressure source 715 for pressuring the lavage fluid and a distal opening 717 in fluid connection with the proximal opening 723 of the entry cannula via tube 793. The entry cannula further has a distal opening 725 disposed within a first cancellous portion of the vertebral body.

The exit cannula further has a proximal opening 733 disposed within a second cancellous portion of the vertebral body. The debris container further comprises a proximal opening 743 in fluid connection with the distal opening 735 of the exit cannula via tube 795. The debris container further comprises a distal opening 745 in fluid connection with the proximal opening 753 of the suction source.

When the pump is activated, the lavage fluid in the lavage fluid container is drawn through the pump and is pressurized and flows through tube 793 into the entry cannula. The lavage fluid exits the entry cannula under high pressure and impacts the soft tissue of the vertebral body. The impact causes the soft tissue to become dislodged from the cancellous bone portion of the vertebral body, thereby debriding the soft tissue and creating a skeleton.

Next, suction source is activated, thereby creating a vacuum at the proximal opening of the exit cannula. Debris produced by the lavage and spent lavage fluid are pulled into this proximal opening and are further drawn into the debris container, where they remain until disposal.

This process continues until the clinician produces a skeleton in the vertebral body.

In some embodiments, the present invention includes a drying device for drying the skeleton portion of the vertebral body.

In some embodiments, the drying device comprises an aspirator.

In some embodiments, the present invention includes a bone cement delivery device. This device delivers cement from outside the vertebral body to the volume inside the skeleton.

Typically, this device comprises longitudinal rod having a longitudinal bore. In some embodiments, the rod comprises first and second end portions having respective entry and exit openings in fluid connection with the bore. In some embodiments, the exit opening opens upon the first end of the rod to produces a linear flow through the rod. In other embodiments, the exit opening opens laterally within the first end portion of the rod to produces a lateral ejection of the bone cement.

Preferably, the rod is made of a biocompatible material such as stainless steel.

In some embodiments, the present invention includes a bone cement injector. This device produces a pressure gradient that delivers cement from the outside of the vertebral body into the skeleton.

In some embodiments, this device comprises a container for containing the bone cement, a pressure source for applying pressure to the bone cement, and an exit port.

In some embodiments, this device is a syringe comprising a barrel having two open ends, a plunger comprising a piston and a rod distally attached to the piston. Preferably, the cement is loaded into the barrel, the plunger is depressed distally and the cement exits through the exit port and enters the vertebral body through the bone cement delivery device.

In some embodiments, the pressure source comprises mechanical advantage. Examples of such pressure sources are found in U.S. Pat. No. 6,348,055 (Preissman), and WO 02/02/064062 (Voellmicke).

In some embodiments, the bone cement applicator includes a tamp having a distal end sized to fit within the delivery device, a longitudinal middle portion, and a proximal end adapted to be gripped. The tamp may be used to urge viscous cement from the bone cement delivery device into the skeleton.

In some embodiments, a tamp and a pressure source may be used together.

The bone paste may be any material typically used to augment vertebral bodies, including bone cements (such as acrylic-based bone cements, such as PMMA-based bone cements), pastes comprising bone particles (either mineralized or demineralized or both; and either autologous, allogenic or both, and ceramic-based bone cements (such as HA and TCP-based pastes)

In some embodiments, the bone paste comprises the bone cement disclosed in Voellmicke above.

In some embodiments, the present invention includes a bone paste pressure relief passage. In the event cement disposed within the skeleton becomes overpressurized, this passage provides the cement with a low pressure path from skeleton to outside the vertebral body.

In some embodiments, a bone cement pressure relief device is disposed within the bone cement pressure relief passage to minimize contact between the pressurized cement and the soft tissue of the vertebral body. Preferred embodiments of this device include those of the bone cement delivery device.

The present invention may be practiced upon any type of vertebral body. In some embodiments, the vertebral body is a human vertebral body. In some embodiments, the human vertebral body comprises a tumor, while in others the human vertebral body is free of tumors. In some embodiments, the vertebral body is intact. In some embodiments, the vertebral body has been fractured. Some fractured vertebral bodies may comprise compression fractures. Some fractured vertebral bodies comprise burst fractures. In some embodiments, the fracture is less than 3 weeks old, while in others the fracture is more than 3 weeks old. In some embodiments, the vertebral body is osteoporotic.

In some embodiments, the present invention produces a vertebral body having a porous cancellous bone structure having an open porosity, wherein the soft tissue contained therein has been removed to produce a skeleton portion. In some embodiments, the open porosity is created by removal of at least 10% of the soft tissue within the region of the open porosity. Preferably, the open porosity is created by removal of at least 25% of the soft tissue within the region of the open porosity, more preferably at least 50%, more preferably at least 95%. Most preferably, the open porosity is created by removal of essentially all of the soft tissue within the region of the open porosity.

Figure 11A:
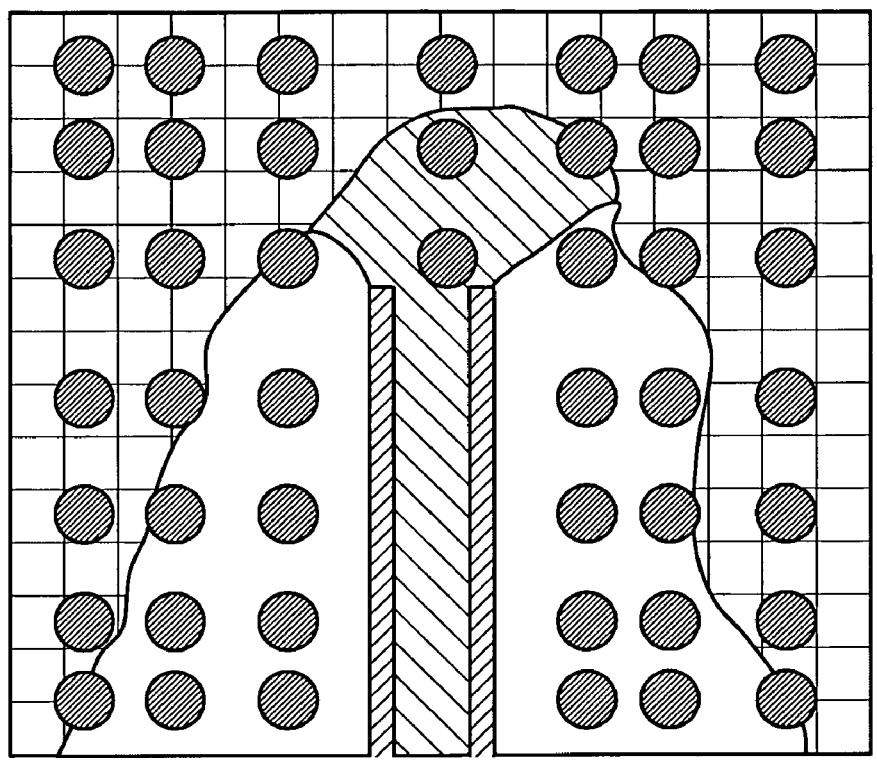
FIGS. 11a-b discloses cross sections of a vertebral body prepared by a preferred procedure in accordance with the present invention.
Figure 11B:
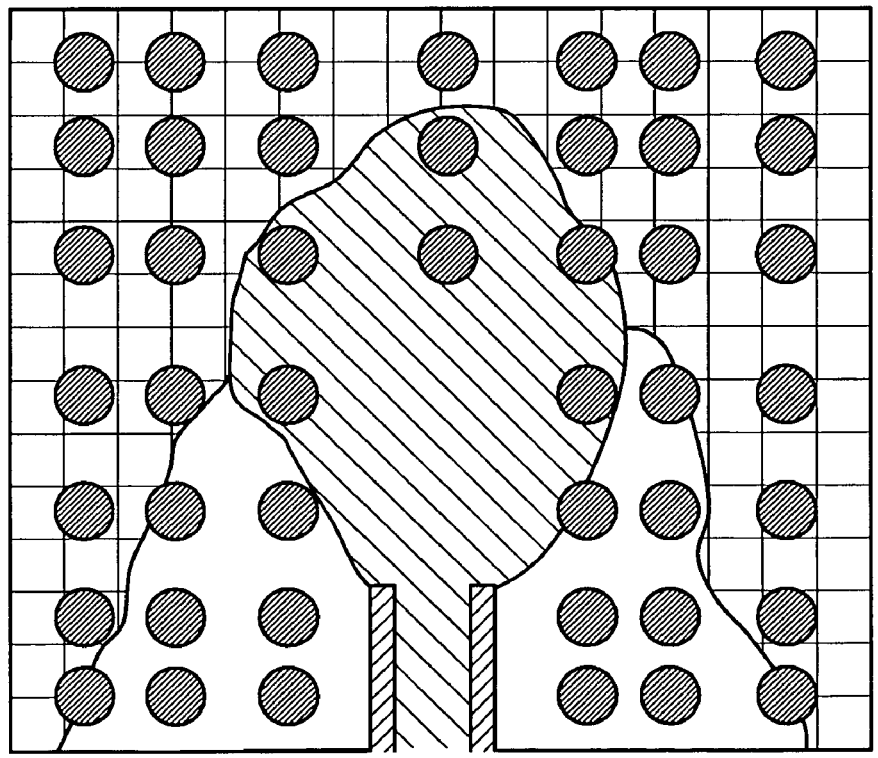
Figure 12:
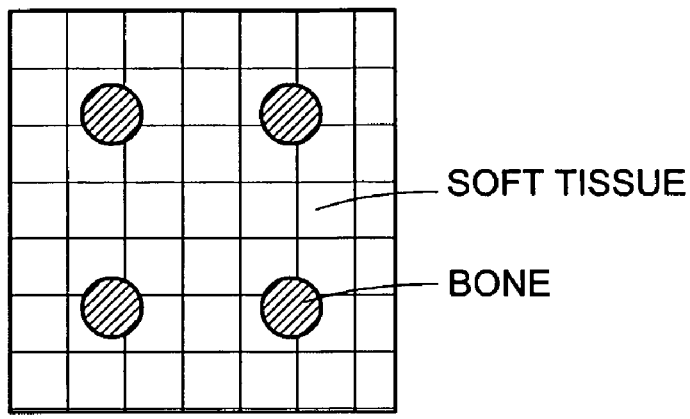
FIG. 12 discloses a cross-section of a portion of a conventional vertebral body.
Figure 13:
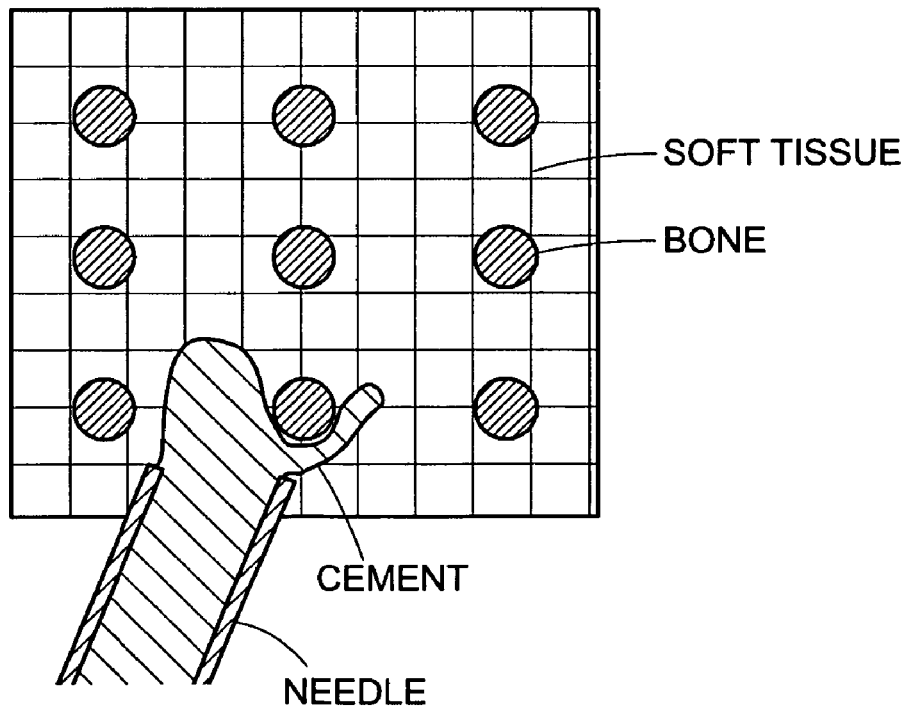
FIG. 13 discloses a cross-section of a conventional procedure comprising the step of filling a conventional vertebral body with a bone paste.

In some embodiments, the middle of the skeleton may be a void. Now referring to FIGS. 11a and b, in some embodiments, the cannula may enter the void and begin depositing bone paste near the distal portion of the skeleton, and then gradually withdraw from the skeleton while continuing to deposit bone paste. The resulting structure has a solid bone paste interior portion and an exterior portion comprising a skeleton interdigitated with bone paste.

Any conventional method of removing either bone marrow or fat may be used in accordance with the present invention. In some embodiments, the soft tissue may be removed by applying suction to the soft tissue contained within the cancellous bone structure of the vertebral body.

In some embodiments, the soft tissue may be removed by applying suction to the soft tissue contained within the cancellous bone structure of the vertebral body. Any conventional methods of applying suction may be used to remove the soft tissue. In some embodiments, a surgical bulb is used. In other embodiments, a conventional syringe is used. In other embodiments, a continuous suction is applied to the soft tissue.

Therefore, in accordance with the present invention, there is provided a structure prepared from a natural vertebral body having a porous cancellous bone structure having bone marrow and fat therein, comprising:

a) a skeleton portion disposed within the porous cancellous bone structure, and b) a bone paste interdigitated within at least a portion of the skeleton portion.

It is believed that the present disclosure comprises the first time that selected disclosed devices have been used in the same procedure.

Therefore, in accordance with the present invention, there is provided a kit for performing vertebroplasty, comprising:
a) a device adapted to create a passage in the vertebral body, and
b) a device adapted to dislodge soft tissue within the vertebral body.

Therefore, in accordance with the present invention, there is provided a kit for performing vertebroplasty, comprising:
a) a device adapted to dislodge soft tissue within the vertebral body, and
b) a device adapted to remove debris within the vertebral body.

Therefore, in accordance with the present invention, there is provided a kit for performing lavage upon a vertebral body, comprising:
a) a device adapted to create a passage in the vertebral body,
b) a lavage device comprising:
   i) a pump having a pressure opening and a suction opening,
   ii) a first cannula adapted to form a first passage in the vertebral body,
   iii) means for fluidly connecting the first cannula to the pressure opening, and
   iv) a second cannula adapted to form a second passage in the vertebral body, and
   v) means for fluidly connecting the second cannula to the suction opening.

Therefore, in accordance with the present invention, there is provided kit for performing lavage upon a vertebral body, comprising:
a) a device adapted to create a passage in the vertebral body,
b) a device adapted to seal an opening in a vessel selected from the group consisting of a vein and an artery, and
c) a bone cement applicator.

Therefore, in accordance with the present invention, there is provided a kit for performing vertebroplasty, comprising:
a) a device adapted to remove debris within the vertebral body, and
b) a device adapted to collect debris removed from the vertebral body.

Therefore, in accordance with the present invention, there is provided a kit for performing vertebroplasty, comprising:
a) a device adapted to remove debris within the vertebral body, and
b) a device adapted to dry the skeleton portion of the vertebral body.

Therefore, in accordance with the present invention, there is provided a kit for performing vertebroplasty, comprising:
a) a device adapted to remove debris within the vertebral body, and
b) a device adapted to dry the skeleton portion of the vertebral body.

I claim:

1. A method of preparing a fractured vertebral body comprising a porous cancellous bone structure having open porosity and interstitial soft tissue contained therein, comprising the steps of:
   a) directing a fluid from a first cannula into the open porosity of the porous cancellous bone structure to dislodge at least a portion of the soft tissue contained therein to create a skeleton,
   b) applying suction to the open porosity to remove the fluid and dislodged soft tissue through a second cannula present within the vertebral body, wherein the first and second cannulae are located at independent locations in the vertebral body and
   c) injecting bone paste into the skeleton.

2. The method of claim 1 wherein step a) is performed by a lavage process.

3. The method of claim 2 wherein the lavage process is a pulsed lavage process.

4. The method of claim 1 wherein step a) creates a skeleton, and wherein the method further comprises the step of:
   c) hemostatically flushing the skeleton.

5. The method of claim 4 further comprising the step of:
   d) flushing the skeleton with saline.

6. The method of claim 5 further comprising the step of:
   e) providing suction to flushed skeleton to remove the saline.

7. The method of claim 1 wherein the fluid has a temperature of at least 42° C.

8. The method of claim 1 wherein the first and second cannulae are independent.

9. The method of claim 1 wherein the first cannula is located in a first pedicle and the second cannula is located in a second pedicle.

* * * * *